United States Patent [19]

Torii et al.

[11] 4,127,454

[45] Nov. 28, 1978

[54] PREPARATION OF BENZOTHIAZOLYLSULFENAMIDES

[75] Inventors: Sigeru Torii; Hideo Tanaka; Masashi Ukida, all of Okayama, Japan

[73] Assignee: Ouchi Shinko Kagaku Kogyo Kabushiki Kaisha, Tokyo, Japan

[21] Appl. No.: 826,794

[22] Filed: Aug. 22, 1977

[30] Foreign Application Priority Data

Oct. 5, 1976 [JP] Japan .................. 51-118981

[51] Int. Cl.$^2$ .................. C25B 3/02; C07D 277/60
[52] U.S. Cl. .................. 204/59 R; 204/72; 204/78; 260/306.6 A
[58] Field of Search .................. 204/59 R, 72, 73 R, 204/7

[56] References Cited

U.S. PATENT DOCUMENTS

| | | | |
|---|---|---|---|
| 2,140,194 | 12/1938 | Yabroff et al. | 204/72 |
| 2,385,410 | 9/1945 | Gardner | 204/72 |
| 3,193,477 | 7/1965 | Baizer | 204/73 A |
| 3,193,484 | 7/1965 | Gleim et al. | 204/79 |

OTHER PUBLICATIONS

Mitin et al., Zh. Obsh. Khimii (Eng. Trans.), vol. 44, No. 9, pt. 2, pp. 2033, 2034, pub. 3/75.
Berge et al., Chemical Abstracts, vol. 82, Abstract 146950z, (1975).

*Primary Examiner*—F.C. Edmundson
*Attorney, Agent, or Firm*—Ladas, Parry, Von Gehr, Goldsmith & Deschamps

[57] ABSTRACT

Benzothiazolylsulfenamides are prepared in a high yield and substantially without a side reaction, via direct electrolytic oxidation, by cross-coupling (1) 2-mercaptobenzothiazole or dibenzothiazyl disulfide or an alkali metal salt of 2-mercaptobenzothiazole with (2) a primary or secondary amine, in the presence of a solvent selected from a dipolar aprotic solvent, a protic solvent, water and mixtures thereof, as well as a supporting electrolyte having adaptability to the solvent.

13 Claims, No Drawings

PREPARATION OF BENZOTHIAZOLYLSULFENAMIDES

BACKGROUND OF THE INVENTION (a) Field of the Invention

This invention relates to a novel process for preparation of benzothiazolylsulfenamides. More Particularly, it relates to a process for preparation of benzothiazolylsulfenamides which comprises cross-coupling, via direct electrolytic oxidation in the presence of a solvent and a suitable supporting electrolyte, 2-mercaptobenzothiazole or dibenzothiazyl disulfide or an alkali metal salt of 2-mercaptobenzothiazole with a primary or secondary amine containing an alkyl group or groups having 2 to 8 carbon atoms or a heterocyclic ring.

(b) Description of the Prior Art

The benzothiazolyslsulfenamides to be used as vulcanization accelerators for rubber have been conventionally prepared by charging into a reactor, 2-mercaptobenzothiazole or dibenzothiazolyl disulfide which is an oxidation product of the benzothiazole, a primary amine such as tert-butyl amine, cyclohexyl amine or a secondary amine such as diethylamine, diisopropylamine, morpholine, and a suitable solvent, and adding thereto an oxidizing reagent such as sodium hypochlorite solution dropwise thereby to effect oxidation. The reaction process may differ somewhat according to the kinds of the amines employed in the reaction.

For example, when cyclohexylamine is used as the amine, a reactor equipped with cooling means is charged with 2-mercaptobenzothiazole, cyclohexyl amine, and water, and the mixture is stirred to form a cyclohexylamine salt of 2-mercaptobenzothiazole. Sodium hypochlorite solution is then added to the reaction mixture dropwise to effect chemical oxidation while the reactor is cooled with water since the reaction is exothermic. The resulting ash-colored or yellowish ash-colored precipitation is subjected to filtration, rinsing with water, dewatering, drying and grinding, to obtain N-cyclohexyl-2-benzothiazolylsulfenamide.

When heterocyclic morpholine is used as the amine, morpholine and a suitable solvent are charged into a reactor, and thereafter sodium hypochlorite solution is added thereto to form morpholine chloride. Then, to the reaction mixture are added dibenzothiazyl disulfide and morpholine, and then sodium perchlorate (an oxidizing reagent) is further added dropwise to effect chemical oxidation. This is followed by removal of morpholine in excess as well as the solvent. The resulting pale brownish yellow precipitation is subjected to filtration, rinsing with water, dewatering, drying, and grinding to obtain N-oxydiethylene-2-benzothiazolylsulfenamide.

Such conventional processes are very complicated since the previous-stage reaction is required before the oxidation reaction. Moreover, the yield is at most about 90% to 93% since a side reaction cannot be avoided in the course of the oxidation reaction. In order to improve the quality of the product and to increase the yield to some extent, it is necessary to simplify the complicated reaction steps accompanied by various production-control problems. Also, it is further necessary to take a measure against waste water pollution caused by side-reaction products as well as small amounts of solvents and the starting amine which could not be recovered or removed and to lower the heavy expenses for a waste water-disposal plant investment as well as the operating cost.

As a result of research, it has now been found that the difficulties of the prior art process can be readily overcome by employing electrolytic oxidation reaction. The present invention is based on this discovery.

SUMMARY OF THE INVENTION

An object of the invention is to provide a novel process for preparation of benzothiazolylsulfenamides via direct electrolytic oxidation reaction of 2-mercaptobenzothiazole, dibenzothiazyl disulfide, or an alkali metal salt of 2-mercaptobenzothiazole with a primary or secondary amine.

Another object of the invention is to provide a novel process for preparation of benzothiazolylsulfenamides of excellent quality, which can be used as vulcanization accelerators, in a high yield and substantially without a side reaction.

These and other objects, features and advantages of the invention will appear more fully from the following detailed description.

According to the present invention, briefly summarized, there is provided a process for preparation of benzothiazolylsulfenamides which comprises cross-coupling, via direct electrolytic oxidation, (1) 2-mercaptobenzothiazol or dibenzothiazyl disulfide or an alkali metal salt of 2-mercaptothiazole with (2) a primary or secondary amine represented by the following formula,

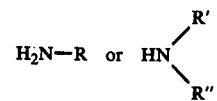

wherein, R is a straight, branched or cyclic alkyl group, and R' and R" independently denote straight, branched or cyclic alkyl groups or a heterocyclic ring in which R' and R" are fused together, said electrolytic oxidation being conducted in the presence of a single or mixed solvent selected from a dipolar aprotic solvent, a protic solvent, and water and a supporting electrolyte adaptable to the solvent selected through the use of electrodes.

DETAILED DESCRIPTION OF THE INVENTION

Reaction scheme

The process according to this invention for preparation of benzothiazolylsulfenamides comprises cross-coupling, via direct electrolytic oxidation, 2-mercaptobenzothiazole or dibenzothiazyl disulfide or an alkali metal salt of 2-mercaptobenzothiazole wherein, the alkali metal is sodium, potassium or lithium with a primary or secondary amine, by applying an electric current at a current density suitable for formation of the benzothiazolylsulfenamides, at a temperature such as room temperature and for a time required to complete the reaction, and employing a suitably selected combination of a solvent, a supporting electrolyte and electrodes, the reaction being illustrated by the following reaction formulas.

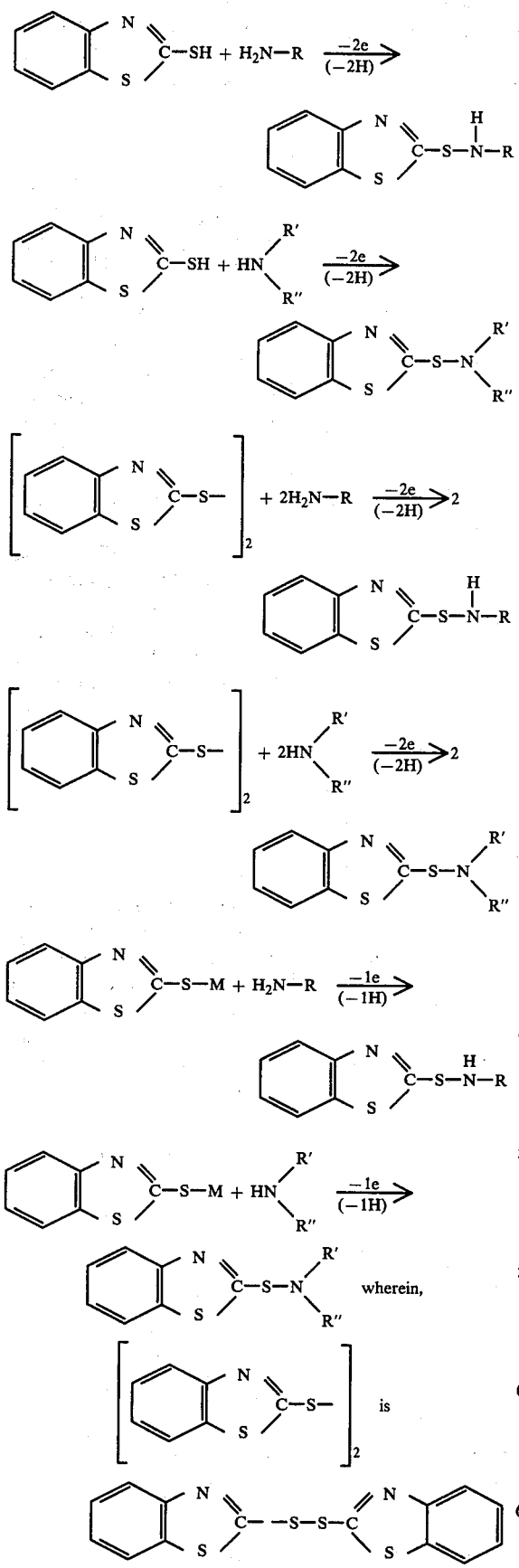

Amine

The primary amines containing a straight, branched or cyclic alkyl group having 3 to 8 carbon atoms to be employed in the present invention typically include n-propylamine, isopropylamine, n-butylamine, tert-butylamine, amylamines, hexylamines, cyclohexylamine, heptylamines, and octylamines. The secondary amines containing straight, branched or cyclic alkyl groups having 2 to 8 carbon atoms, or heterocyclic groups, typically include diethylamine, di-n-propylamine, diisopropylamine, di-n-butylamine, di-tert-butylamine, pyrrolidine, piperidine, and morpholine. The amines to be employed in the present invention, however, are not restricted to these amines.

Solvent

The solvents to be employed in the present invention can be conveniently classified into three solvent groups; i.e., dipolar aprotic solvents as the first group, protic solvents except water as the second group, and water as the third group. A mixture of the two or three solvents selected from these solvent groups can also be employed in the present invention.

The dipolar aprotic solvents of the first group typically include acetonitrile; methylene chloride; nitrobenzene; dimethylformamide; tetrahydrofuran; aliphatic or aromatic tertamines such as pyridine, picolines, dimethylaniline, and trialkylamines having 1 to 6 carbon atoms in each of the alkyls; dimethylsulfoxide, and hexamethylphosphoroamide. The protic solvents of the second groups typically include monohydric and polyhydric alcohols of 1 to 4 carbon atoms in the hydrocarbyl group such as methanol, ethanol, tert-butyl alcohol, ethylene glycol, 2-methoxy-ethanol, and 2-ethoxyethanol; aliphatic and aromatic primary amines and secondary amines such as aniline, monomethylaniline, mono- and dialkylamines having 1 to 8 carbon atoms in each of the alkyls, and alkanolamines having 2 to 6 carbon atoms each of the alkanol groups. The solvent is generally employed in such an amount as to prepare a homogeneous reaction solution or suspension.

Supporting electrolyte

The supporting electrolytes to be employed in combination with the solvent of the first group in the invention are represented by perchlorate salts such as alkali metal, alkaline earth metal or quaternary ammonium salts, e.g. lithium perchlorate, magnesium perchlorate, and quaternary alkylammonium perchlorates; tetrafluoroborate salts such as quaternary alkylammonium tetrafluoroborates; quaternary alkylammonium halides; alkali metal halides; nitrates such as quaternary ammonium nitrate; and para-toluenesulfonates such as quaternary alkylammonium para-toluenesulfonates; wherein, the alkyl group is methyl, ethyl or a propyl, the alkali metal is lithium, sodium or potassium, and the halogen is chlorine, bromine or iodine.

The supporting electrolytes to be employed in combination with the protic solvents of the second group include alkali metal salts of alkanoic acid of 1 to 3 carbon atoms such as formic acid, acetic acid, propionic acid; salts of lower alkanoic acids such as alkali metal and ammonium salts, e.g. ammonium acetate; and trialkylamines having 1 to 3 carbon atoms in each of the alkyls such as trimethylamine, triethylamine, and a tripropylamine, as well as the above-mentioned electrolyte to be employed in combination with the first-group solvents wherein the alkali metal is lithium, sodium or potassium.

Examples of the supporting electrolytes to be employed with water include neutral salts such as halides, sulfates, and nitrates of alkali metals as well as bases such as alkalimetal hydroxides wherein the alkali metal is lithium, sodium, or potassium, and the halogen is chlorine, bromine or iodine. When a mixture of two or three solvents selected from the above-mentioned solvent groups is employed, the suitable supporting electrolyte can be selected from the suitable electrolytes corresponding to any of the solvent groups.

Electrodes

Any commercial electrode for electrolysis can be employed for the electrodes in the present invention. Examples of suitable electrodes are electrodes made of platinum, carbon, various steel plates, nickel, and metal oxide materials such as titanium oxide, with or without having been subjected to any suitable pre-treatment.

The solvents, supporting electrolytes and electrodes to be employed in the present invention are not restricted to those exemplified above.

Electrolytic oxidation

The electrolytic oxidation reaction according to the present invention can typically be carried out by adding, to a mixture of 2-mercaptobenzothiazole and about 1.1 times the mol quantity (of the benzothiazole) of a primary or secondary amine or a mixture of dibenzothiazyl disulfide and about 2.5 times the mol quantity of a primary or secondary amine or a mixture of an alkali metal salt of 2-mercaptobenzothiazole and about 1.1 times the mol quantity of a primary or secondary amine, a suitable quantity of a selected solvent and a supporting electrolyte corresponding to the solvent, the quantity of the electrolyte being about 1 to 60%, preferably about 1 to 20% by weight of 2-mercaptobenzothiazole, dibenzothiazyl disulfide or an alkali metal salt of 2-mercaptobenzothiazole. The primary or secondary amine can be generally employed in a stoichiometrically excess amount.

In the present invention, particular conditions of electrolytic oxidation depend on the combination of types of the solvent and supporting electrolyte and the type of electrodes, but those skilled in the art can readily arrive at suitable conditions thereof. In the present invention, direct current is generally employed, but alternating current may also be used if so desired. The electric current density to be applied is generally in the range of about 0.1 to 100 mA/cm$^2$ and preferably in the range of about 1 to 20 mA/cm$^2$. The terminal voltage is generally in the range of about 1 to 50 V. The reaction is carried out at around room temperature, preferably at a temperature of about 15° to about 30° C. The quantity of electricity to be passed is generally in the range of about 1 to about 10 F/mol, preferably in the range of about 2 to about 6 F/mol (Faraday/mol of the product). The reaction is preferably carried out under stirring. The treatment following termination of reaction depends on the solvent and supporting electrolyte employed in the reaction. In general, benzothiazolylsulfenamides in the form of crystals having an appearance inherent thereto can be obtained either by cooling the resulting reaction liquid in an ice freezing mixture (e.g., ice-sodium chloride) to precipitate crystals and then filtering off the resulting solid product under reduced pressure, or by distilling away the solvent under reduced pressure from the resulting reaction liquid and then subjecting the residue to rinsing with water or column chromatography to remove the supporting electrolyte, these steps then being followed by distilling away of the liquid content and then drying of the residue.

Advantageous features and utility of the present invention

A conventional process for preparation of benzothiazolylsulfenamides is conducted via a pure chemical reaction and not via electrochemical reaction, and, therefore, a side reaction may not be avoided in such a conventional process. Thus, benzothiazolylsulfenamides are obtained in a yield of about 90 to 93%. The conventional process entails a further problem in that dibenzothiazolyl disulfide, which is more expensive than 2-mercaptobenzothiazole, must be employed when some kinds of amines are used in the reaction.

In contrast, in accordance with the process of the present invention, no or little side reaction takes place since the reaction is carried out at approximately room temperature, and an added supporting electrolyte remains unchanged. Thus, benzothiazolylsulfenamides can be obtained in a very high yield of about 99%. Moreover, 2-mercaptobenzothiazole, which is less expensive than dibenzothiazyl disulfide, can be employed to obtain excellent results irrespective of the kinds of amines selected for the cross-coupling. According to the present invention, benzothiazolylsulfenamides can also be readily produced from dibenzothiazyl disulfide or an alkali metal salt of 2-mercaptobenzothiazole.

According to the conventionl process, moreover, there are produced side reaction products, and environmental pollution could be caused by the waste water containing small amounts of the starting amines and solvents which could not have been recovered. Such problems have been eliminated according to the present invention since little side reaction takes place, and the filtrate and solvent distilled away can be recycled to the electrolytic reaction. Thus, this invention provides a desirable industrial process for preparation of benzothiazolylsulfenamides.

In order to indicate more fully the nature and utility of this invention, the following examples of practice are set forth, it being understood that these examples are presented as illustrative only and are not intended to limit the scope of the invention.

EXAMPLE 1

Preparation of N-cyclohexyl-2-benzothiazolylsulfenamide

A test tube with a side arm, 50 ml in capacity, is equipped with a stirrer, a thermometer and platinum electrodes (2cm × 3 cm in dimension). In this tube are placed 150 mg (0.90 millimol) of 2-mercaptobenzothiazole, 0.11 ml (0.96 millimol) of cyclohexylamine (primary amine), and 100 mg of tetraethylammonium perchlorate (supporting electrolyte), followed by 20 ml of simple-distillation dimethylformamide (dipolar aprotic solvent) to make the mixture a homogeneous solution.

Electrolysis of this solution is carried out under stirring at a temperature of 29° to 30° C., at a terminal voltage of 1.7 to 2.0V, and at a current density of 2 to 4 mA/cm$^2$. After passing a quantity of electricity of 6F/mol, the solvent is distilled away under reduced pressure from the reaction liquid. The residual liquid is dissolved in benzene, passed through a silica gel column, and then concentrated. Thus, in one instance of practice, 237 mg of N-cyclohexyl-2-benzothiazolylsulfenamide having a melting point of 98° C. in the form of grey-white powdery crystals was obtained in a yield of 99%.

As a result of identification by infrared (IR) absorption and nuclear magnetic resonance (NMR) absorption spectra as well as the mixed examination by using an authentic sample, the product was confirmed to be N-cyclohexyl-2-benzothiazolylsulfenamide.

EXAMPLE 2

Preparation of N-oxydiethylene-2-benzothiazolylsulfenamide

The following process was carried out according to the method set forth in Example 1. To a mixture of 150 mg (0.90 millimol) of 2-mercaptobenzothiazole and 0.1 ml (1.14 millimols) of morpholine (secondary amine) were added 100 mg of lithium perchlorate as a supporting electrolyte and 20 ml of dimethylformamide as a dipolar aprotic solvent to make the mixture a homogeneous solution.

Electrolytic reaction of this solution was carried out by using carbon electrodes (1.5 cm × 4 cm in dimension), under stirring at a reaction temperature of 15° to 20° C., at a terminal voltage of 1.8 to 2.0V, and at a current density of 3 to 5 mA/cm$^2$. After passing a quantity of electricity of 5 F/mol, the reaction liquid was treated in the same way as in Example 1 to obtain 224 mg (99% yield) of N-oxydiethylene-2-benzothiazolylsulfenamide in the form of pale yellow-brown crystals having a melting point of 81° C.

As a result of identification by IR absorption and NMR absorption spectra as well as the mixed examination with an authentic sample, the product was confirmed to be N-oxydiethylene-2-benzothiazolylsulfenamide.

EXAMPLE 3

Preparation of N,N-dicyclohexyl-2-benzothiazolylsulfenamide

The following process was carried out according to the method specified in Example 1. To a mixture of 150 mg (0.90 millimol) of 2-mercaptobenzothiazole and 0.2 ml (1.00 millimol) of dicyclohexylamine (secondary amine) were added 50 mg of sodium bromide (supporting electrolyte) and 25 ml of methanol (protic solvent) to make the mixture a homogeneous solution.

Electrolytic reaction of this solution was carried out with platinum electrodes (2 cm × 3 cm in dimension), under stirring at a temperature of 24° to 26° C., at a terminal voltage of 2.0 V, and at a current density of 5 to 10 mA/cm$^2$ by passing a quantity of electricity of 5F/mol. The reaction liquid was concentrated by reducing its volume to about one half and was then cooled. The separated crystals were filtered off, rinsed with water, and dried to obtain 310 mg (99% yield) of N-dicyclohexyl-2-benzothiazolylsulfenamide, of a melting point of 102° C., in the form of grey-white powdery crystals. As a result of identification by IR and NMR absorption spectra as well as the mixed examination with an authentic sample, the product was confirmed to be N,N-dicyclohexyl-2-benzothiazolylsulfenamide.

EXAMPLE 4

Preparation of N,N-diethyl-2-benzothiazolylsulfenamide

The following process was carried out according to the method of Example 1. A homogeneous solution was prepared by mixing 167 mg (1.00 millimol) of 2-mercaptobenzothiazole, 50 mg of ammonium bromide (supporting electrolyte), and 20 ml of diethylamine (a secondary amine, protic solvent).

Electrolytic reaction of this solution was carried out with carbon electrodes (1.5 cm × 4 cm in dimension), under stirring at a temperature of 15° to 27° C., at a terminal voltage of 2.0 V, and at current density of 3 to 7 mA/cm$^2$. After passing a quantity of electricity of 5 F/mol, the resulting reaction liquid was treated in the same way as in Example 3 to obtain 235 mg (99% yield) of N,N-diethyl-2-benzothiazolylsulfenamide, of a density of 1.17 g/cm$^3$, in the form of a dark-brown liquid. The product was confirmed to be N,N-diethyl-2-benzothiazolylsulfenamide as a result of identification by IR and NMR absorption spectra and elemental analysis (as $C_{11}H_{14}N_4S_2$):

Calculated: C55.4%, H 5.9%, N 11.7%; Found: C55.5%, 6.0%, N 11.5%.

EXAMPLE 5

Preparation of N-tert-butyl-2-benzothiazolylsulfenamide

The following process was carried out in accordance with the method of Example 1. To a mixture of 167 mg (1.00 millimol) of 2-mercaptobenzothiazole and 0.125 ml (1.20 millimols) of tert-butylamine (a primary amine) were added 100 mg of sodium hydroxide (a supporting electrolyte) and 20 ml of water to prepare a homogeneous solution.

Electrolytic reaction of this solution was carried out with platinum electrodes (2 cm × 3 cm in dimension), under stirring at a reaction temperature of 20° to 22° C., at a terminal voltage of 2.0 V, and at a current density of 5 to 10 mA/cm$^2$. After passing a quantity of electricity of 6F/mol, precipitated crystals were filtered off from the reaction liquid, rinsed with water, and dried to obtain 235 mg (99% yield) of N-tert-butyl-2-benzothiazolylsulfenamide, of a melting point of 107° C., in the form of ash-colored powdery crystals. As a result of identification by IR and NMR absorption spectra as well as the mixed examination with an authentic sample, the product was confirmed to be N-tert-butyl-2-benzothiazolylsufenamide.

EXAMPLE 6

Preparation of N-tert-octyl-2-benzothiazolylsulfenamide

The following process was carried out according to the method of Example 1. To a mixture of 167 mg (1.00 millimol) of 2-mercaptobenzothiazole and 153 ml (1.20 millimols) of tert-octylamine (a primary amine) were added 100 mg of potassium hydroxide as a supporting electrolyte and 20 ml of water to prepare a homogeneous solution.

Electrolytic reaction of this solution was carried out with steel plate (SUS27) electrodes (2.0 cm × 3.0 cm in dimension), under stirring at a reaction temperature of 25° to 28° C., at a terminal voltage of 2.0V, and at a current density of 5 to 10 mA/cm$^2$ by passing a quantity of electricity of 6F/mol. The resulting reaction liquid was treated as in Example 5 to obtain 292 mg (99% yield) of N-tert-octyl-2-benzothiazolylsulfenamide, of a melting point of 100° C., in the form of yellow powdery crystals. As a result of identification by IR and NMR absorption spectra as well as the mixed examination with an authentic sample, the product was confirmed to be N-tert-octyl-2-benzothiazolylsulfenamide.

EXAMPLE 7

Preparation of N,N-diisopropyl-2-benzothiazolylsulfenamide

The following process was carried out in accordance with the method of Example 1. To a mixture of 167 mg (1.00 millimol) of 2-mercaptobenzothiazole and 0.17 ml (1.20 millimols) of diisopropylamine (secondary amine) were added 100 mg of sodium bromide as a supporting electrolyte and 20 ml of water to prepare a homogeneous solution.

Electrolytic reaction of this solution was carried out with carbon electrodes (1.5 cm × 4 cm in dimension) under stirring at a reaction temperature of 23° to 26° C., at a terminal voltage of 2.1V, and at a current density of 2 to 7 mA/cm$^2$ by passing a quantity of electricity of 6F/mol. The resulting reaction liquid was treated as in Example 5 to obtain 164 mg (99% yield) of N-diisopropyl-2-benzothiazolylsulfenamide, of a melting point of 57° C., in the form of pale yellow-grey powdery crystals. As a result of identification by IR and NMR absorption spectra as well as the mixed examination with an authentic sample the product was confirmed to be N,N-diisopropyl-2-benzothiazolylsulfenamide.

EXAMPLE 8

Preparation of N-cyclohexyl-2-benzothiazolylsulfenamide

The following process was conducted in accordance with the method of Example 1. To a mixture of 150 mg (0.45 millimol) of dibenzothiazyl disulfide and 147 mg (1.49 millimols) of cyclohexylamine (a primary amine) were added 100 mg of tetraethylammonium perchlorate as a supporting electrolyte and 20 ml of dimethylformamide as a dipolar aprotic solvent to prepare a homogeneous solution.

Electrolytic reaction of this solution was carried out with platinum electrodes (2 cm × 3 cm in dimension) under stirring at a reaction temperature of 26° to 28° C., at a terminal voltage of 2.0V, and at a current density of 15 to 20 mA/cm$^2$. After passing a quantity of electricity of 6F/mol, the resulting reaction liquid was treated as in Example 1, to obtain 256 mg (98% yield) of N-cyclohexyl-2-benzothiazylsulfenamide, of a melting point of 98.1° C., in the form of ash-colored powdery crystals. As a result of identification by IR and MMR) absorption spectra as well as mixed examination with authentic samples, the product was confirmed to be N-cyclohexyl-2-benzothiazolylsulfenamide.

EXAMPLE 9

Preparation of N-cyclohexyl-2-benzothiazolylsulfenamide

The following process was conducted in accordance with the method of Example 1. To a mixture of 171 mg (0.90 millimol) of sodium salt of 2-mercaptobenzothiazole and 85 mg (0.97 millimol) of cyclohexylamine (primary amine) were added 100 mg of tetraethylammonium perchlorate as a supporting elecyrolyte and a mixed solvent consisting of 15 ml of dimethylformamide as a dipolar aprotic solvent and 5 ml of water, to prepare a homogeneous solution.

Electrolytic reaction of this solution was carried out with platinum electrodes (2 cm × 3 cm in dimension) under stirring at a reaction temperature of 25° to 30° C., at a terminal voltage of 2.0 to 3.0 V, and at a current density of 2 to 10 mA/cm$^2$. After passing a quantity of electricity of 6F/mol, the resulting reaction liquid was treated as in Example 1, to obtain 237 mg (99% yield) of N-cyclohexyl-2-benzothiazolylsulfenamide, of a melting point of 98° C., in the form of grey-white powdery crystals. As a result of identification by IR and NMR absorption spectra as well as the mixed examination with an authentic sample, the product was confirmed to be N-cyclohexyl-2-benzothiazolylsulfenamide.

As clearly shown by these examples, the present process for preparation of benzothiazolylsulfenamides comprises cross-coupling, via direct electrolytic oxidation, 2-mercaptobenzothiazole or dibenzothiazyl disulfide or an alkali metal salt of 2-mercaptobenzothiazole with a primary or secondary amine. Thus, benzothiazolylsulfenamides of superior quality can be obtained in higher yields, by a simple reaction process and without a side reaction.

We claim:

1. A process for preparation of benzothiazolylsulfenamides, which comprises cross-coupling, via direct electrolytic oxidation, a member selected from the group consisting of 2-mercaptobenzothiazole, dibenzothiazyl disulfide and an alkali metal salt of 2-mercaptobenzothiazole wherein the alkali metal is sodium, potassium or lithium with a primary or secondary amine represented by the formula

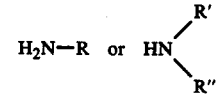

wherein, R is a straight, branched or cyclic alkyl group having 3 to 8 carbon atoms, and R' and R'' represent a straight, branched or cyclic alkyl group having 2 to 8 carbon atoms, respectively, or a heterocyclic ring in which R' and R'' are fused together, said electrolytic oxidation being conducted in the presence of a solvent selected from the group consisting of dipolar aprotic solvents, protic solvents, water and mixtures thereof, and a supporting elecyrolyte adaptable to the solvent by using electrodes thereby to produce the benzothiazolylsulfenamide 2. The process as set forth in claim 1, in which the electrolytic oxidation reaction is carried out at approximately room temperature by applying an electric current at a current density suitable for formation of benzothiazolylsulfenamides for a time required to complete the reaction.

3. The process as set forth in claim 1, in which the amine represented by the formula,

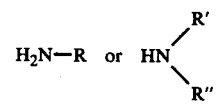

is selected from the group consisting of n-propylamine, isopropylamine, n-butylamine, tert-butylamine, amylamines, hexylamines, cyclohexylamine, heptylamine, octylamines, diethylamine, di-n-propylamine, diisopropylamine, di-n-butylamine, di-tert-butylamine, diamylamines, dihexylamines, dicyclohexylamine, diheptylamines, dioctylamines, and morpholine.

4. The process as set forth in claim 1, in which the solvent is selected from the group consisting of acetonitrile, methylene chloride, nitrobenzene, dimethylformamide, tetrahydrofuran, pyridine, tert-amines, dimethylsulfoxide, hexamethylphosphoroamide, alcohols, primary amines, secondary amines, water, and mixtures thereof.

5. The process as set forth in claim 1, in which the supporting electrolyte to be used in the presence of a dipolar aprotic solvent or a protic solvent is a member selected from the group consisting of alkali metal and alkaline earth metal perchlorates and alkali metal halides wherein the alkali metal is lithium, sodium or potassium, and the halogen is chlorine, bromine or iodine.

6. The process as set forth in claim 1, in which the supporting electrolyte to be used in the presence of a dipolar aprotic solvent or a protic solvent is a quaternary alkyl-ammonium salt of an acid selected from the group consisting of perchloric acid, nitric acid, para-toluene sulfonic acid and hydrohalogenic acids wherein the alkyl is methyl, ethyl or a propyl and the halogen is chlorine, bromine or iodine.

7. The process as set forth in claim 1, in which the supporting electrolyte to be used in the presence of a dipolar aprotic solvent or a protic solvent is selected from the group consisting of lithium perchlorate, magnesium perchlorate, quaternary alkylammonium perchlorate, quaternary alkylammonium tetrafluoroborates, quaternary alkylammonium halides, alkali metal halides, quaternary ammonium nitrate, and quaternary alkylammonium para-toluenesulfonates.

8. The process as set forth in claim 1, in which the supporting electrolyte to be used in the presence of a protic solvent is selected from the group consisting of alkali metal and ammonium salts of alkanoic acids and amines.

9. The process as set forth in claim 1, in which the supporting electrolyte to be used in the presence of water is selected from the group consisting of halides, sulfates, and nitrates of alkali metals and alkali metal hydroxides.

10. The process as set forth in claim 1, in which the electrode is made of a material selected from the group consisting of platinum, carbon, steels, nickel, and metal oxides.

11. The process as set forth in claim 1, in which the primary or secondary amine is employed in the electrolytic oxidation reaction in a stoichiometrically excess amount.

12. The process as set forth in claim 1, in which the supporting electrolyte is employed in the electrolytic oxidation reaction in a quantity of the order of 1 to 60% by weight of 2-mercaptobenzothiazole, dibenzothiazyl disulfide, or an alkali metal salt of 2-mercaptobenzothiazole.

13. The process as set forth in claim 1, in which the electrolytic oxidation reaction is carried out at an electric current density of the order of 0.1 to 100 mA $cm^2$ by passing a quantity of electricity of the order of 2 to 10 F/mol.

* * * * *